United States Patent [19]

Laghi

[11] Patent Number: 5,133,754
[45] Date of Patent: Jul. 28, 1992

[54] MULTI HARDNESS SILICONE IMPLANTS

[76] Inventor: Aldo A. Laghi, 13 Meridian La., Ballston LK., N.Y. 12019

[21] Appl. No.: 672,727

[22] Filed: Mar. 21, 1991

[51] Int. Cl.$^5$ .......................... A61F 2/02; A61F 2/12; A61F 2/18; A61F 2/28
[52] U.S. Cl. ........................... 623/11; 623/16; 623/8; 623/10
[58] Field of Search ............... 623/8, 10, 12, 16, 11

[56] References Cited

U.S. PATENT DOCUMENTS

| | | | |
|---|---|---|---|
| D. 290,877 | 7/1987 | Giampapa et al. | 623/16 X |
| 3,720,959 | 3/1973 | Hahn | 623/16 |
| 4,344,191 | 8/1982 | Wagner | 623/16 |
| 4,597,763 | 7/1986 | Schwelkhart | 623/8 |
| 4,755,411 | 7/1988 | Wing et al. | 264/45.8 X |
| 4,764,169 | 8/1988 | Grendahl | 623/6 |
| 4,773,909 | 9/1988 | Chaglassian | 623/8 |
| 4,778,466 | 10/1988 | Brotman | 623/10 |
| 4,818,829 | 4/1989 | Nopper et al. | 264/247 X |
| 4,938,234 | 7/1990 | Capriotti | 623/10 X |
| 4,990,160 | 2/1991 | Terino | 623/16 X |

FOREIGN PATENT DOCUMENTS 2124500 2/1984 United Kingdom .................. 623/6

Primary Examiner—David Isabella
Assistant Examiner—Elizabeth M. Burke
Attorney, Agent, or Firm—Joseph C. Mason, Jr.; Ronald E. Smith

[57] ABSTRACT

Silicone rubber implants having at least two integral and inseparable sections separated by a line of demarcation where the hardness of the different sections is different so that the implant more closely mimics the human body part it simulates. A chin implant has a first hard section and a second soft section. The hard section abuts the patient's mandible when the implant is installed and the soft part provides the patient with a soft chin. A nose implant is softest at its tip to simulate a natural nose and is harder in the dorsum area and harder still in the columella area. The implants are made by injecting a first batch of silicone rubber having a first hardness into a first mold, followed by transfer of the completed part to a second mold and injection of at least a second batch of silicone having a differing hardness into the second mold, onto the first-formed part, so that the materials of differing hardness bond naturally to one another. Coinjection techniques may also be employed to achieve the same result.

4 Claims, 1 Drawing Sheet

MULTI HARDNESS SILICONE IMPLANTS

TECHNICAL FIELD

This invention relates, generally, to silicone rubber implants of the type used in cosmetic and reconstructive surgery. More particularly, it relates to implants of non-uniform hardness

BACKGROUND ART

Silicone rubber is the material of choice for implants because it does not react to the human body and the body does not react to it. Moreover, it is easily molded into any desired shape and holds its shape in perpetuity.

Chin implants made of silicone are well known. In U.S. Pat. No. 4,713,077 to Small, a silicone chin implant is combined with a biologically acceptable metal for securing the implant. Significantly, the consistency of the silicone is uniform throughout the implant.

A silicone rubber breast implant is shown in U.S. Pat. No. 3,681,787 to Perras; as in the Small device, the silicone rubber part of the implant has a uniform consistency.

There are numerous other patents and publications disclosing differing prosthetic devices for implanting in differing parts of the body, and all of them share a common structural feature: all parts of the respective implants have the same hardness as all other parts thereof.

Prior to the filing of this disclosure, no worker in the field of silicone rubber implants had considered the desirability of the known structures. Everyone knows that the tip of the human nose is soft and flexible, and that the columella and dorsum parts thereof are hard, for example, but the art of prosthetic devices has failed to address the implications of this fact. The present inventor is the first, anywhere in the world, to observe the unsatisfactory nature of the presently available devices, said unsatisfactory nature being a result of the uniform hardness of the devices. An individual fitted with a silicone rubber nose, for example, has a hard columella and an equally hard dorsum, which is suitable and satisfactory, but has an equally hard nose tip, which is not. Similarly, the tip or leading end of a human chin is relatively soft, but a prosthetic chin made by known methods is equally hard at all locations.

The prior art, when considered as a whole in accordance with the requirements of law, neither teaches nor suggests to those of ordinary skill in this art how the limitations thereof could be overcome.

DISCLOSURE OF INVENTION

The longstanding but heretofore unfulfilled need for a device that is not subject to the limitations of the earlier devices is now fulfilled by a silicone rubber implant that has differing degrees of hardness throughout its structure. A novel method of making the multi hardness implant is also disclosed.

A chin implant is provided that is stiff at the points thereof that contact the mandible to which it is mounted, and which has reduced stiffness on the outer parts thereof. The result is an implant that has the look and feel of a natural chin. This achievement represents a significant breakthrough in the art of prosthetic devices. A nose implant is also disclosed; it is soft where its corresponding human part is soft and is hard where its corresponding part is hard. Although additional implants are not shown, in order to limit the length of this disclosure to a practical length, it is abundantly clear that the teachings and suggestions of this disclosure have additional applications and that the number of applications is limited only by the number of prosthetic devices in existence. Accordingly, the claims of this breakthrough invention are broadly cast so as to include all silicone rubber implants having at least two different degrees of hardness.

The primary object of this invention is to pioneer the art of multi hardness silicone rubber implants.

Another important object is to disclose a novel method whereby implants having more than one degree of hardness may be economically manufactured.

These and other important objects, advantages and features of the invention will become apparent as this description proceeds.

The invention accordingly comprises the features of construction, combination of elements and arrangements of parts that will be exemplified in the construction set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the drawings, in which.

Similar reference numerals refer to similar parts throughout the several views of the drawings.

BEST MODES FOR CARRYING OUT THE INVENTION

Figure 1:
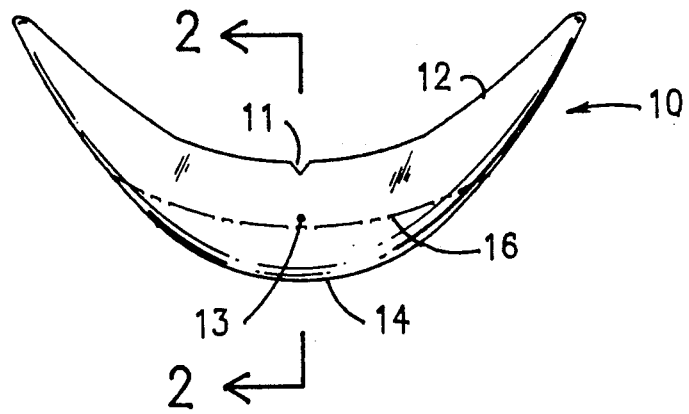
FIG. 1 is a plan view of a chin implant made in accordance with the teachings of this invention.

Referring now to FIG. 1, it will there be seen that an exemplary embodiment of the invention is denoted as a whole by reference numeral 10.

Chin implant 10 has two integrally formed sections; inner section 12 has a first predetermined hardness and outer section 14 has a second predetermined hardness. Arcuate line 16 is the line of demarcation between sections 12 and 14 but it should be understood from the outset that said line does not represent a parting line and that the novel method of making device 10, as set forth hereinafter, produces a device of unitary construction. More specifically, the harder rubber of section 12 has a slightly different appearance than the softer rubber of section 14, and the purpose of line 16 is simply to point out said difference in appearance. No difference in appearance is readily visible under casual inspection of implant 10, but a distinction in appearance between sections 12 and 14 can be ascertained when implant 10 is positioned between the observer's eye and a source of bright light.

Notch 11 facilitates conforming implant 10 to the curvature of the bone structure underneath. The implant is usually stitched to the fascia (muscle tissue), although it could be fastened to the bone.

In a contemplated commercial embodiment of the present invention, inner section 12 has a Shore A hardness rating between forty to sixty and outer section 14 has a Shore A hardness rating between ten to twenty five. Thus, inner section 12, which abuts the mandible of the patient when properly implanted, is firm; this is desirable because such firmness facilitates its positioning relative to the mandible. Outer section 14, however, is soft; this is desirable because a natural chin is soft at the location occupied by said outer section 14.

Figure 2:
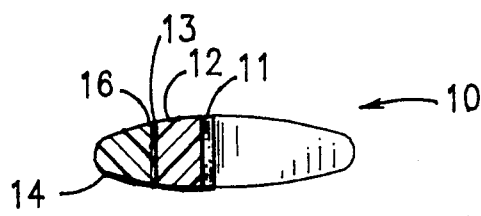
FIG. 2 is a sectional view taken along line 2—2 in FIG. 1.

Point 13 in FIG. 1 represents an injection of a silicone polymer compound having a high concentration of tantalum carbide. This compound provides high radio-opacity under x-rays and thus facilitates x-ray inspection of the implant. In a frontal view, point 13 would appear as a line; it appears as a line in the sectional view of FIG. 2.

Figure 3:
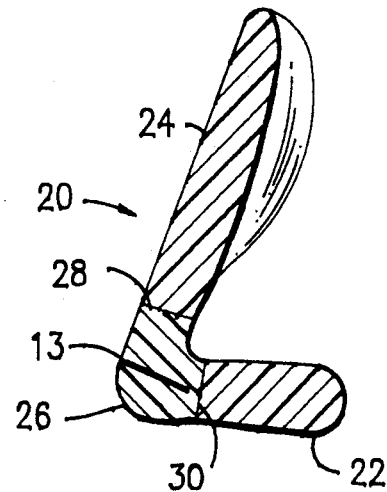
FIG. 3 is a sectional view taken along line 3—3 in FIG. 5.
Figure 4:
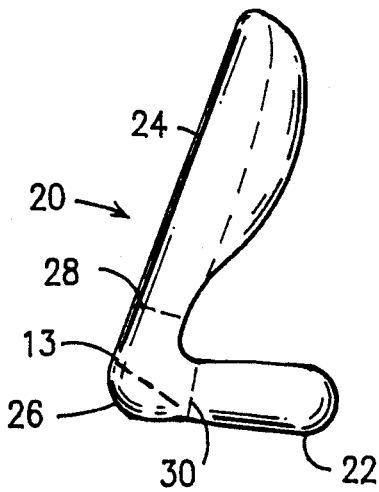
FIG. 4 is a side elevational view of the nose implant shown in FIG. 3.
Figure 5:
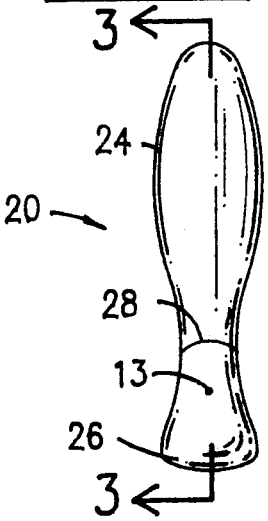
FIG. 5 is a front elevational view of the nose implant.

FIGS. 3–5 depict a nose implant 20 having a first section or columella 22 with a first predetermined hardness, a second section or dorsum 24 with a second predetermined hardness, and a third section or nose tip 26 with a third degree of hardness. Demarcation lines 28 and 30 are visible under good lighting conditions but the three sections of the novel implant 20 are integrally formed and inseparable from one another. The nose implant may also include injection 13 for radio opacity. The columella section 22 has the highest hardness rating of the three sections, and the nose tip section 26 has the lowest hardness rating of the three sections. The dorsum section 24 has an intermediate hardness rating. Thus, the respective hardness ratings mimic their human counterparts and give the patient a prosthetic device far superior to the devices heretofore known. It is believed that the respective Shore A hardness of tip 26, dorsum 24, and columella 22 should be about 10, 40, and 60, respectively, plus or minus about 5.

Novel methods for making the novel implants will now be disclosed.

In a first method, silicone rubber having a first preselected hardness is first injected into a first mold to form the first section of the chin or other implant. The completely formed first section is then placed in a second mold and silicone rubber having a second preselected hardness is immediately thereafter injected into the second mold, in overlying relation to the first-injected section. By selecting the proper formulae for the two silicone rubber compounds, a natural bond is formed between the two sections of different hardnesses. A third mold and a third silicone rubber compound is used where a nose implant is to be made, and so on.

In a second method, silicone rubber of two differing hardnesses is injected into a preselected mold simultaneously, using coinjection techniques. This method also results in formation of a natural bond between the materials of differing hardnesses.

Either of these two methods may be followed when making implants having three of more different hardnesses.

Significantly, no adhesives are used in the manufacturing process. The natural bond between the silicone materials having differing degrees of hardness ensures that the sections will not separate from one another.

This invention is clearly new and useful. Moreover, it was not obvious to those of ordinary skill in this art at the time it was made, in view of the prior art considered as a whole in accordance with the requirements of law.

It will thus be seen that the objects set forth above, and those made apparent from the foregoing description, are efficiently attained and since certain changes can be made in the above description without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A prosthetic device of the type implanted below the skin of a human individual for cosmetic or reconstructive purposes, comprising:
   a first section made of a preselected material having a first predetermined hardness;
   said first section having an arcuate configuration so that it abuts a patient's mandible when said device is implanted;
   said first predetermined hardness being about 20 Shore A;
   a second section made of said preselected material having a second predetermined hardness different from said first predetermined hardness;
   said second section having an arcuate configuration so that it provides a natural appearance in an chin when said device is implanted;
   said second predetermined hardness being about 40 Shore A.

2. The device of claim 1, wherein said preselected material is silicone rubber.

3. A prosthetic device of the type implanted under the skin of a human individual for cosmetic or reconstructive purposes, comprising:
   a first section made of a preselected material having a first predetermined hardness;
   said first section having a predetermined configuration that provides the shape of a tip area of a nose when the device is implanted;
   a second section made of a preselected material having a second predetermined hardness greater than the hardness of said first section;
   said second section having a predetermined configuration that provides the shape of a dorsum area of a nose when the device is implanted;
   a third section made of a preselected material having a third predetermined hardness greater than the hardness of said second section;
   said third section having a predetermined configuration that provides the shape of a columella area of a nose when the device is implanted;
   said first, second, and third sections being integrally formed with one another to provide the shape of a nose when the device is implanted.

4. The device of claim 3, wherein said preselected material is silicone rubber.

* * * * *